US005510111A

United States Patent [19]

Grimberg

[11] Patent Number: 5,510,111
[45] Date of Patent: *Apr. 23, 1996

[54] THERAPEUTIC COMPOSITION REMEDYING THE DISORDERS APPEARING IN THE OTOLARYNGOLOGICAL SPHERE

[76] Inventor: Georges S. Grimberg, 123 rue de l'Université, 75007 Pais, France

[ * ] Notice: The term of this patent shall not extend beyond the expiration date of Pat. No. 5,128,141.

[21] Appl. No.: 400,171

[22] Filed: Mar. 6, 1995

Related U.S. Application Data

[63] Continuation of Ser. No. 182,222, Jan. 14, 1994, abandoned.

[30] Foreign Application Priority Data

Jan. 28, 1993 [FR] France .................................. 93 00861

[51] Int. Cl.⁶ ..................................................... A61K 9/00
[52] U.S. Cl. .......................... 424/439; 424/705; 514/725; 514/849
[58] Field of Search ................................ 514/725, 7, 849, 514/725; 424/439, 705

[56] References Cited

U.S. PATENT DOCUMENTS 5,128,141  7/1992  Grimberg .................................. 424/451

FOREIGN PATENT DOCUMENTS 2431863  2/1980  France .

OTHER PUBLICATIONS

European Journal of Haematology, vol. 40, No. 5, May, 1988.
The Journal of Cancer Research and Clinical Oncology, vol. 116, No. 5, 1990.

Primary Examiner—D. Gabrielle Phelan
Attorney, Agent, or Firm—Kirschstein et al.

[57] ABSTRACT

The new therapeutic composition remedying the disorders appearing in the otolaryngological sphere comprises a very large quantity of vitamin A per dose, each dose containing 40,000 to 60,000 IU of vitamin A for a treatment of three to four days.

6 Claims, No Drawings

THERAPEUTIC COMPOSITION REMEDYING THE DISORDERS APPEARING IN THE OTOLARYNGOLOGICAL SPHERE

This application is a continuation of U.S. patent application Ser. No. 08/182,222, filed Jan. 14, 1994, now abandoned.

FIELD AND BACKGROUND OF THE INVENTION

The invention relates to new therapeutic composition remedying the disorders appearing in the otolaryngological sphere.

Therapeutic compositions formed of associations of vitamins A and of various active principles having a therapeutic activity in order to fight disorders appearing in the otolaryngological sphere are already known.

The medicament disclosed in FR-A-2,228,470 contains vitamin A, sulphur, cystin and yeast. Its prescription is of 900,000 IU of vitamin A for fifteen days. This therapy which is recommended for fifteen to twenty days per month during three months makes the patient to absorb a quantity of vitamin A of 2,700,000 IU, at least.

In order to reinforce the immunity against rhinitis, a risk is shown which is widely superior to the benefit, mainly for women when they are pregnant. Three months of treatment are presently unthinkable.

Likewise, FR-A-2,647,784 discloses a new therapeutic composition of vitamin A, but at a physiological dose, and it does not meet the conditions necessary for a treatment of an acute or influenzal rhinitis.

Actually, in therapeutics, the problem which is posed today is called BENEFIT-RISK and becomes the real base for any medicament.

In case of an acute or influenzal rhinitis, it has appeared that one has to intervene strongly and quickly during a very short period for the BENEFIT-RISK to be positive.

In this case, the side reactions are practically non existent and this is particularly the case for women under oral contraceptive product.

SUMMARY OF THE INVENTION

The present invention contains a high dose of vitamin A which is twice to three times the dose of the medicament disclosed in FR-A-2,228,470 and from twenty to thirty times superior to the medicament disclosed in FR-A-2,647,784, and the duration of the treatment is from three to four days, the result being that there is no risk, and that a rhinitis heals within three to four days.

DESCRIPTION OF THE PREFERRED EMBODIMENT

According to the invention, the new therapeutic composition is characterized by a very large quantity of vitamin A per dose, each dose containing from 40,000 to 60,000 IU of vitamin A.

According to another feature of the invention, one dose contains:

| | |
|---|---|
| Vitamin A | 40,000 to 60,000 IU |
| L. Cystin base | 217.8 mg |
| Washed sublimed sulphur | 66 mg |
| Dead yeast | 232.2 mg |

The new therapeutic composition in which the organic sulphur (L. Cystin base) is added to the washed sublimed sulphur, and which contains dead yeast which is most often a saccharomyces type yeast, has given the following results:

First group: Twenty patients suffering from an acute rhinitis have been treated with three doses of the medicament 40,000 IU per day for four days.

Second group: Twenty patients suffering from an acute rhinitis have been treated with three doses during four days, corresponding to the therapeutic composition disclosed in FR-A-2,228,470.

Third group: Twenty patients suffering from an acute rhinitis have been treated with three doses during four days, corresponding to the therapeutic composition disclosed in FR-A-2,647,784.

The twenty patients of the first group treated with the formula of the new medicament are the only ones who were cured within four days.

It has consequently been concluded that the clinical tests have proved the improvement the new formula, which acts in a strong and quick manner within a very short period, thereby becoming the cure-all of acute rhinitis and therefore of the immunostimulation in a general manner for a quick answer.

I claim:

1. A method of treating a patient suffering from acute rhinitis, consisting of the administration to the patient of a therapeutic composition comprising from 40,000 to 60,000 IU of Vitamin A per dose, L. Cystine base, washed sublimed sulphur and dead yeast.

2. A method according to claim 1, wherein the patient is administered three doses of the composition per day.

3. A method according to claim 1, wherein the patient is administered three doses of the composition per day for three to four days.

4. A method according to claim 3, wherein the patient is administered three doses of the composition per day for four days.

5. A method according to claim 1, wherein said dead yeast is a saccharomyces yeast.

6. A method according to claim 1 wherein said composition comprises per dose:

| | |
|---|---|
| Vitamin A | 40,000 to 60,000 IU |
| L. Cystine base | 217.8 mg |
| Washed sublimed sulphur | 66 mg |
| Dead yeast | 232.2 mg. |

* * * * *